(12) United States Patent
Cheng et al.

(10) Patent No.: US 8,753,380 B2
(45) Date of Patent: Jun. 17, 2014

(54) SEPARABLE PEDICLE SCREW

(75) Inventors: Liming Cheng, Shanghai (CN); Yan Yu, Shanghai (CN); Zhili Zeng, Shanghai (CN); Wei Xu, Putuo District (CN); Yongwei Jia, Shanghai (CN); Lie Qian, Shanghai (CN); Rui Zhu, Shanghai (CN); Jianjie Wang, Shanghai (CN); Zhourui Wu, Shanghai (CN)

(73) Assignee: Tongji University, Shanghai (CN)

( * ) Notice: Subject to any disclaimer, the term of this patent is extended or adjusted under 35 U.S.C. 154(b) by 0 days.

(21) Appl. No.: 13/376,440

(22) PCT Filed: Aug. 2, 2010

(86) PCT No.: PCT/CN2010/075630
§ 371 (c)(1),
(2), (4) Date: Dec. 6, 2011

(87) PCT Pub. No.: WO2012/016369
PCT Pub. Date: Feb. 9, 2012

(65) Prior Publication Data
US 2013/0131737 A1    May 23, 2013

(51) Int. Cl.
*A61B 17/86*    (2006.01)
(52) U.S. Cl.
USPC .......................................... 606/306; 606/331
(58) Field of Classification Search
USPC ..................... 411/2; 606/305, 306, 316, 331
See application file for complete search history.

(56) References Cited

U.S. PATENT DOCUMENTS

| 5,971,987 A | 10/1999 | Huxel et al. |
| 6,267,025 B1 | 7/2001 | Sand et al. |
| 2006/0058796 A1 | 3/2006 | Hartdegen et al. |
| 2006/0081553 A1 | 4/2006 | Patterson et al. |
| 2006/0149263 A1* | 7/2006 | Newcomb et al. ............... 606/73 |
| 2010/0036430 A1 | 2/2010 | Hartdegen et al. |
| 2011/0015684 A1* | 1/2011 | Belcheva et al. ............... 606/314 |
| 2011/0184471 A1* | 7/2011 | Foley et al. .................... 606/286 |

FOREIGN PATENT DOCUMENTS

| CN | 101366656 A | 2/2009 |
| DE | 35 38 593 A1 | 5/1987 |
| EP | 323429 A1 | 7/1989 |

(Continued)

OTHER PUBLICATIONS

Chen C S, Chen W J, Cheng C K, et al. Failure analysis of broken pedicle screws on spinal instrumentation [J]. Med Eng Phys, 2005, 27 (6) : 487-496.
Gaines ,Robert WJR. The use of pedicle-screw internmal fixation for the operative treatment of spinal disorders [J]. The Journal of Bone and Joint Surgery (AM) ,2000 ,82 (10) :1458-1476.

(Continued)

*Primary Examiner* — Christian Sevilla
(74) *Attorney, Agent, or Firm* — Knobbe, Martens, Olson & Bear, LLP

(57) ABSTRACT

Techniques are generally described related to a method and system for treating an injury with a bone screw. One example bone screw may be configured to fracture at a pre-selected frangible location so that the point of failure is not in an inaccessible location, e.g., deeply embedded below the surface of a treated bone. The bone screw may further include a material disposed over the frangible location that is designed to temporarily strengthen the screw and selected to be absorbed by the body over a period of time after installation of the screw in the bone. One example bone screw may include an unthreaded portion that is configured to facilitate removal of an embedded screw fragment from a bone in the event that the screw fails in vivo.

6 Claims, 6 Drawing Sheets

(56) References Cited

FOREIGN PATENT DOCUMENTS

| FR | 2 625 430 A | 7/1989 |
| FR | 2 825 015 A1 | 5/2001 |
| JP | 1214359 A | 8/1989 |
| WO | WO 2006031692 A | 3/2006 |
| WO | WO 2008060765 | 5/2008 |

OTHER PUBLICATIONS

PCT Search Report and Written Opinion dated May 12, 2011 in Application No. PCT/CN2010/075630.

Website—Scient'x Alphatec Spine—Thoraco-Lumbar Fixation, http://www.scientx.com/product_thoracolumbarfixation_isobarttl.php, printed on Oct. 21, 2011.

* cited by examiner

US 8,753,380 B2

SEPARABLE PEDICLE SCREW

REFERENCE TO RELATED APPLICATIONS

This application is the U.S. National Phase entry under 35 U.S.C. §371 of International Application PCT/CN2010/075630, filed Aug. 2, 2010, entitled "SEPARABLE PEDICLE SCREW," the entirety of which is incorporated herein by reference.

BACKGROUND

Unless otherwise indicated herein, the approaches described in this section are not prior art to the claims in this application and are not admitted to be prior art by inclusion in this section.

Bone screws have been used in spinal instrumentation since the 1960s to manage bone fractures and correct deformity. For example, the pedicle screw may provide a means of gripping a spinal segment, where the screw acts as a firm anchor point in one vertebra that can be connected to other such anchor points in other vertebrae with a rod. With two or more consecutive vertebrae fixated by such a construct, motion between the vertebrae is prevented, which assists in spinal fusion procedures by holding bony structures together. Many surgeons also believe that pedicle screws enhance patient recovery because they provide immediate stability for the spine and early mobilization for the patient.

SUMMARY

In accordance with one embodiment of the disclosure, a bone screw includes a shank, a threaded portion formed on an end of the shank, a frangible region formed in the shank, and an unthreaded portion disposed between the threaded portion and the frangible portion, wherein the unthreaded portion is configured to facilitate removal of the threaded portion of the screw from a bone when the frangible portion of the screw has broken after installation of the screw in the bone.

In accordance with another embodiment of the disclosure, a pedicle screw includes a shank, a threaded portion formed on an end of the shank, and an unthreaded portion disposed in a center portion of the shank, wherein the unthreaded portion is configured to facilitate removal of the threaded portion of the screw from a bone.

In accordance with a further embodiment of the disclosure, a method for treating an injury includes selecting a bone screw having a threaded portion formed on an end of a shank, a frangible region formed in the shank, and an unthreaded portion disposed between the threaded portion and the frangible portion, wherein the unthreaded portion is configured to facilitate removal of the threaded portion of the screw from the bone when the frangible portion of the screw has broken after installation of the screw in the bone, and installing the screw into a bone.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
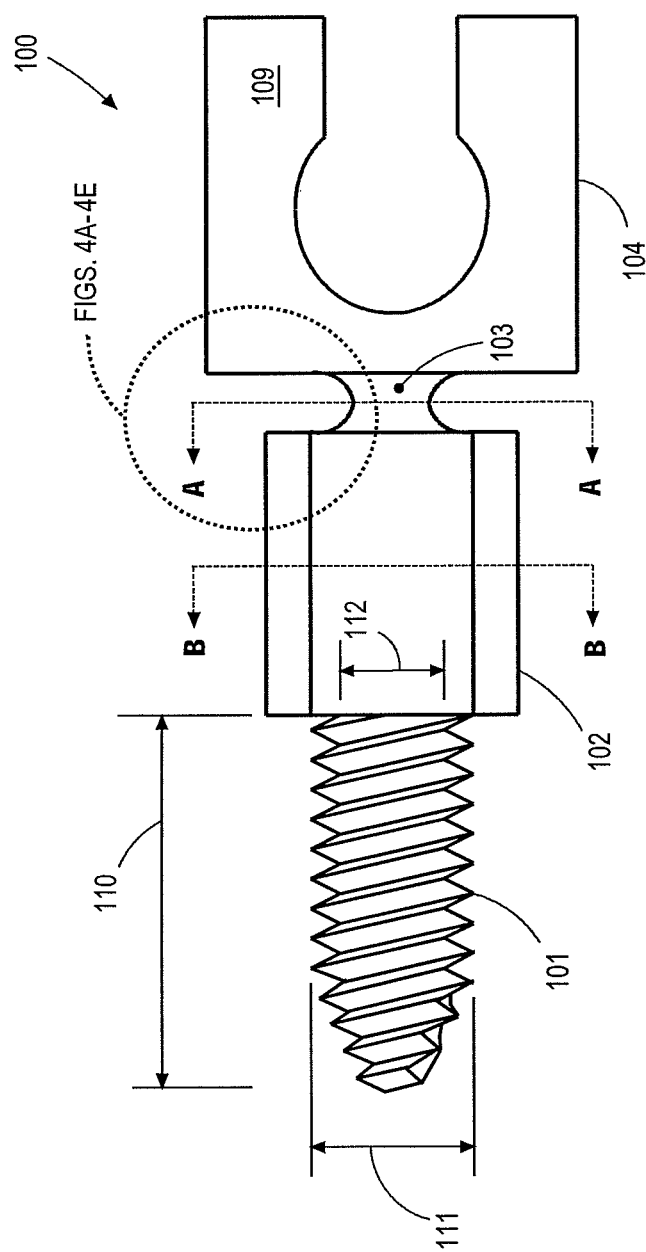
FIG. 1 shows a schematic diagram of an illustrative embodiment of a bone screw.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the disclosure, as generally described herein, and illustrated in the Figures, can be arranged, substituted, combined, and designed in a wide variety of different configurations, all of which are explicitly contemplated and make part of this disclosure.

While bone screws have long been used for a large number of applications, some drawbacks are known. For example, bone screws are typically left in place permanently to avoid the complications that may arise from reoperative surgery. Over time, such screws may fracture and fail, requiring removal. Because the point of failure of a bone screw is commonly in a threaded portion of the screw or at a junction between a threaded portion and an unthreaded portion of the screw, the broken screw fragment, i.e., the screw tip, can be deeply embedded in the now-healed bone material. Removal of such a screw fragment can involve enlarging the bony tunnel around the screw fragment to provide access to the fragment, possibly causing excessive loss of bone mass and/or bone fracture. Alternatively, the screw fragment may have to remain in the bone, which can be physiologically and psychologically problematic for the patient.

Embodiments disclosed herein contemplate a bone screw configured to simplify the removal of the screw in the event that the screw fails in vivo. According to some embodiments, a bone screw may be configured to fracture at a pre-selected frangible location so that the point of failure is not in an inaccessible location, e.g., deeply embedded below the surface of a treated bone. The bone screw may further include a material disposed over the frangible location that is designed to temporarily strengthen the screw and selected to be absorbed by the body over a period of time after installation of the screw in the bone. According to some embodiments, a bone screw may include an unthreaded portion that is configured to facilitate removal of an embedded screw fragment from a bone in the event that the screw fails in vivo.

FIG. 1 shows a schematic diagram of an illustrative embodiment of a bone screw 100. Bone screw 100 may include a threaded portion 101 formed on a tip thereof, an unthreaded portion 102, a frangible portion 103, and a head 104. Head 104 may be a typical bone screw head. For example, when bone screw 100 is a pedicle screw used to anchor two or more consecutive spine segments together, head 104 may include a clamp fixture 109 for mechanically coupling a connecting rod to bone screw 100. Bone screw 100 may be constructed of stainless steel or other durable surgical-grade materials, such as titanium and titanium-containing alloys.

Threaded portion 101 may be formed into the shank of bone screw 100 and may be substantially similar in configuration to the threaded portion of traditional pedicle screws. To wit, in some embodiments, threaded portion 101 may be self-tapping to simplify installation and/or may have a thread depth that increases toward the tip to enhance pullout strength. A length 110 and major diameter 111 of threaded portion 101 may vary depending on the size of bone into which bone screw 100 will be installed and the desired depth of placement of bone screw 100. For example, length 110 and major diameter 111 may be smaller for installation in smaller bones, such as the thoracic vertebrae, than for installation in larger bones, such as the lumbar and sacral vertebrae.

Unthreaded portion 102 may be formed into the shank of bone screw 100 adjacent to threaded portion 101 and is configured to facilitate removal of threaded portion 101 from a bone if bone screw 100 fails in vivo after installation. For example, in some embodiments, unthreaded portion 102 may include at least one pair of flat and substantially parallel sides, thereby providing gripping surfaces for unscrewing threaded portion 101 from a bone when threaded portion 101 is completely embedded in a bone. In some embodiments, as shown in FIG. 1, unthreaded portion 102 may have a cross section having a polygonal shape, e.g., square, triangular, hexagonal, etc., so that a sleeved tool configured to fit the cross-section of the unthreaded portion 102 can be used to unscrew threaded portion 101 from a bone when threaded portion 101 is completely embedded in a bone.

Figure 2A:
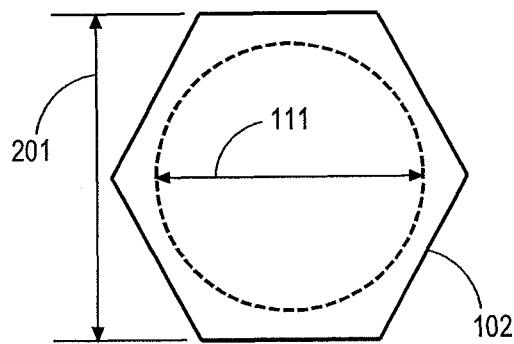
FIGS. 2A-E show cross-sectional views of illustrative embodiments of the bone screw in FIG. 1, taken from section B-B.

FIGS. 2A-E show cross-sectional views of illustrative embodiments of bone screw 100, taken from section B-B in FIG. 1. In FIG. 2A, unthreaded portion 102 is hexagonal in cross section and has a width 201 that is substantially wider than major diameter 111. Such a hexagonal cross section facilitates the use of an inner-hexagon sleeved tool to unscrew threaded portion 101 after bone screw 100 has failed and head 104 has separated from unthreaded portion 102. Unthreaded portion 102 can be used to greatly simplify the removal of threaded portion 101 even when threaded portion 101 is completely embedded in a bone, since such a procedure does not require removal of bone material surrounding threaded portion 101. In addition, because a width 201 of the hexagonal cross section of unthreaded portion 102 is wider than major diameter 111, unthreaded portion 102 is configured to mechanically interfere with the circular opening formed in a bone by threaded portion 101, thereby acting as a mechanical stop that prevents unthreaded portion 102 from being deeply embedded in a bone during installation of bone screw 100. In such an embodiment, unthreaded portion 102 can be readily accessed without the need for removing a significant amount of bone material.

Figure 2B:
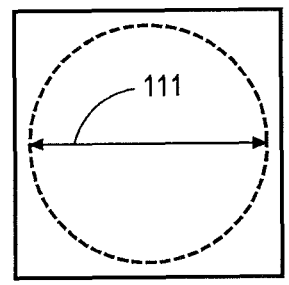
Figure 2C:
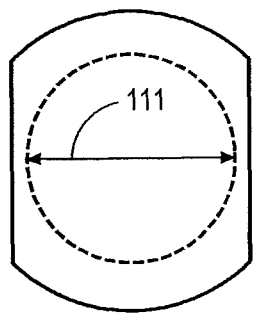
Figure 2D:
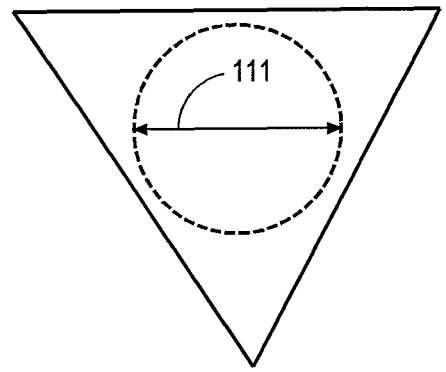

In FIGS. 2B-2D, the cross section of unthreaded portion 102 is illustrated as having other geometric shapes, specifically a square, a circle having two substantially parallel flats, and a triangle, respectively. In such embodiments, the cross-sectional shape of unthreaded portion 102 may be mated to a sleeved tool configured with an appropriately shaped inner-sleeve. Other geometrical shapes for the cross-section of unthreaded portion 102 are also contemplated, such as star drives or other shapes that can be mated to a corresponding sleeved tool. As shown in FIGS. 2B-2D, the cross section of unthreaded portion 102 may be configured to interfere with a circular opening in a bone formed by having a diameter equal to the major diameter of the threaded portion, thereby acting as a mechanical stop that prevents unthreaded portion 102 from being deeply embedded in a bone during installation of bone screw 100.

Figure 2E:
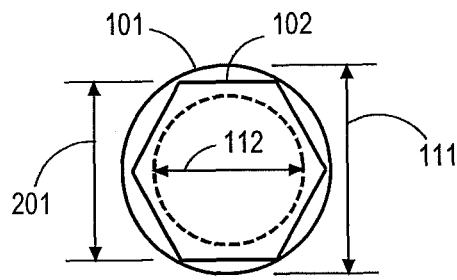

In other embodiments, unthreaded portion 102 may be configured to have a width or diameter that is substantially equal to major diameter 111, but larger than a minor diameter 112 of threaded portion 101, so that unthreaded portion 102 does not act as a mechanical stop against a bone during installation of bone screw 100. FIG. 2E illustrates one such embodiment. Because unthreaded portion 102 does not act as a mechanical stop against a bone during installation of bone screw 100, unthreaded portion 102 may be embedded partially in the bone.

Figure 3:
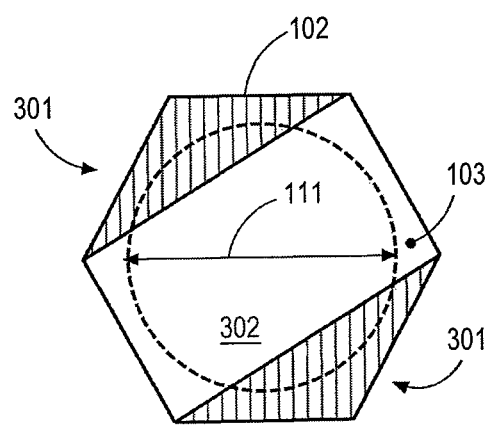
FIG. 3 shows a cross-sectional view of an illustrative embodiment of the bone screw in FIG. 1, taken from section A-A, in which a frangible portion is a reduced-cross-sectional portion of the shank of the bone screw.
Figure 4A:
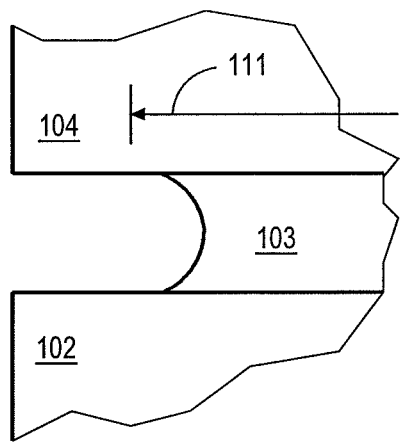
FIGS. 4A-D show expanded schematic views of illustrative embodiments of the frangible region indicated in FIG. 1, where the frangible region is an annular ring.
Figure 4B:
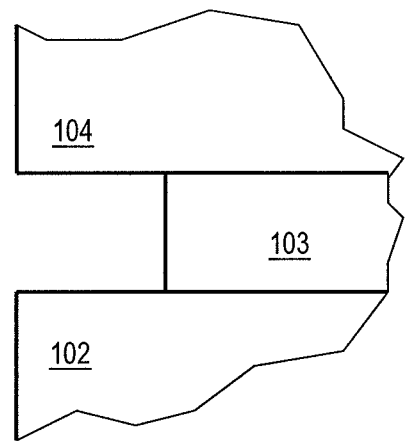
Figure 4C:
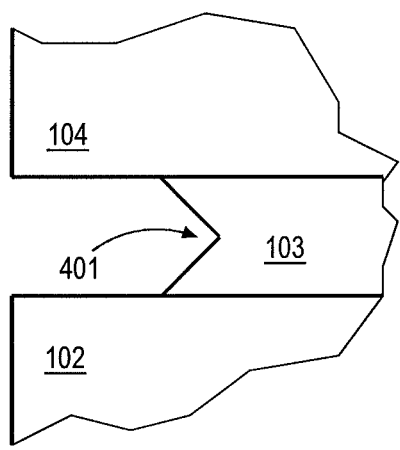
Figure 4D:
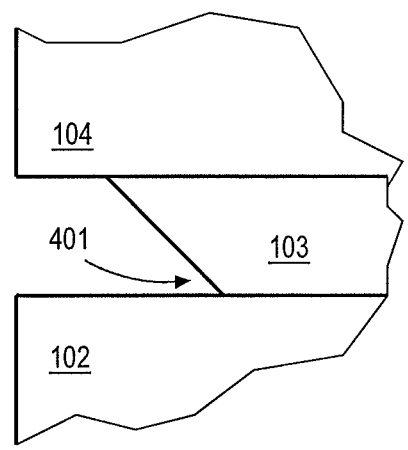

Referring back to FIG. 1, frangible portion 103 may be formed in the shank of bone screw 100 so that if, over time, bone screw 100 fails, the point of failure may be at frangible portion 103, rather that at a portion of bone screw 100 that is embedded in bone and relatively inaccessible. Frangible portion 103 may be disposed between head 104 and unthreaded portion 102, so that if bone screw 100 fails, threaded portion 101 and unthreaded portion 102 will make up one fragment of bone screw 100. Consequently, such a fragment can be readily removed by using unthreaded portion 102 to unscrew the fragment from the bone. In some embodiments, frangible portion 103 is a reduced-cross-section portion of the shank of bone screw 100. FIG. 3 shows a cross-sectional view of an illustrative embodiment of bone screw 100, taken from section A-A, in which frangible portion 103 is a reduced-cross-section portion of the shank of bone screw 100. In FIG. 3, the unhatched area 302 indicates the cross-section of frangible portion 103 and hatched areas 301 indicate the difference in cross-sectional area between unthreaded portion 102 and frangible portion 103, for example where material may have been removed from the shank of bone screw 100 to form unhatched area 302 and frangible portion 103. In such an embodiment, frangible portion 103 may have a lower cross-sectional area than the cross-sectional area of unthreaded portion 102 and/or the cross-sectional area of threaded portion 101. In some embodiments, frangible portion 103 may have a cross-sectional area that is approximately 90% or less than the cross-sectional area of unthreaded portion 102. In some embodiments, frangible portion 103 may have a cross-sectional area that is less than the area of a circle having a diameter equal to major diameter 111. In some embodiments, frangible portion 103 may have a cross-sectional area that is less than the area of a circle having a diameter equal to minor diameter 112. In such embodiments, the reduced cross-sectional area of frangible region 103 greatly increases the likelihood of bone screw 100 failing at frangible region 103 rather than at an inaccessible region of threaded portion 101. In addition, the fact that frangible region 103 is positioned closer to the midpoint of bone screw 100 than threaded portion 101 is to the midpoint of bone screw 100 further increases the likelihood that any mechanical failure of bone screw 100 will take place at frangible region 103. The hatched regions in FIG. 3 illustrate only one example of how frangible region 103 may have a reduced-cross-sectional area with respect to unthreaded portion 102 and/or threaded portion 101. In some embodiments, frangible region 103 may be an annular ring formed in unthreaded portion 102. FIGS. 4A-D show expanded schematic views of illustrative embodiments of frangible region 103 indicated in FIG. 1, where frangible region 103 is an annular ring. In FIG. 4A, the annular ring that makes up frangible region 103 has a semi-circular profile. For reference, major diameter 111 of threaded portion 101 is included in FIG. 4A. As shown, the diameter for frangible region 103 may be significantly less than major diameter 111 to increase the likelihood that the failure point of bone screw 100 will be frangible region 103, rather than a region of threaded portion 101. In FIG. 4B, the annular ring that makes up frangible region 103 has a rectangular profile. In FIGS. 4C and 4D, the annular ring that makes up frangible region 103 has a profile that includes a triangular in-cut 401 that may act as a scribe mark. Since the mode of failure of bone screw 100 is typically a fatigue failure, in-cut 401 may further increase the likelihood that any failure of bone screw 100 will take place at frangible region 103.

According to some embodiments, bone screw 100 may include a material designed to temporarily strengthen bone screw 100, where the material is selected to be absorbed by the body over a period of time after installation of the screw in the bone. The absorbable material may be disposed over frangible region 103 to structurally support the portion of bone screw 100 that is weakened by the presence of frangible region 103. In such embodiments, the absorbable material reinforces bone screw 100 during the time that bony structures anchored together by one or more bone screws 100 fuse together and increase in structural strength. As the treated bony structures become stronger, bone screw 100 is slightly weakened in frangible region 103 because the absorbable material is slowly absorbed by the body of the patient. Consequently, once the treated bony structures have healed, frangible region 103 may be slightly weakened so that the failure point of bone screw 100 will be in the desired location. The one or more absorbable materials disposed over frangible region 103 may be selected based on mechanical properties, i.e., modulus of elasticity, etc., and absorbability by the human body. Example absorbable materials include calcium phosphate and calcium sulphate.

Figure 5:
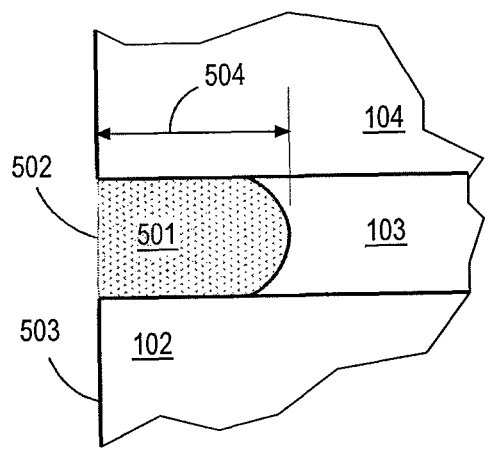
FIG. 5 shows an expanded schematic view of an illustrative embodiment of the frangible region indicated in FIG. 1, in which an absorbable material is disposed over the frangible region.

FIG. 5 shows an expanded schematic view of an illustrative embodiment of frangible region 103 indicated in FIG. 1, in which an absorbable material 501 is disposed over frangible region 103. In some embodiments, absorbable material 501 is disposed over frangible region 103 so that a surface 502 is formed that is substantially flush with adjacent surface 503 of unthreaded portion 102. In some embodiments, the depth 504 of a feature forming frangible region 103 may be selected based on the absorbability of absorbable material 501 by the human body. Specifically, for a relatively fast-absorbing material, frangible region 103 may be configured with a depth 504 so that absorbable material 501 is not completely absorbed for six to eight months after installation of bone screw 100. Thus, the absorption time of absorbable material 501 may be determined for bone screw 100 by the configuration of frangible region 103. Alternatively, in other embodiments absorbable material 501 may be selected based on the geometry of frangible region 103. Thus, the absorption time of absorbable material 501 may be determined for bone screw 100 by the specific absorbable material 501 selected for bone screw 100.

Figures 6, 7:
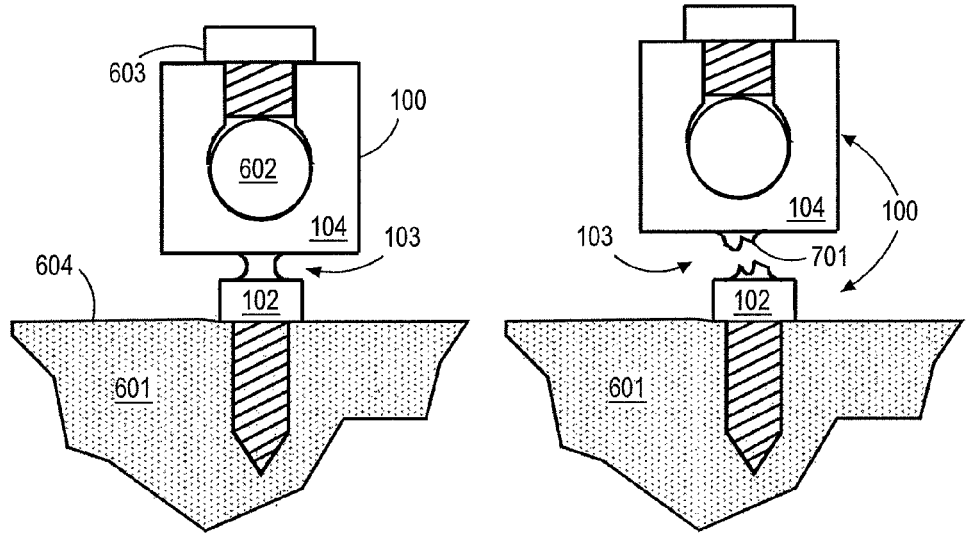
FIG. 6 shows a schematic view of an illustrative embodiment of a bone screw installed in a bony structure.
FIG. 7 shows a schematic view of an illustrative embodiment of a bone screw installed in a bony structure after a frangible region of the bone screw has broken.

In operation, bone screw 100 may be inserted into a bony structure, such as a pedicle bone of a thoracic, sacral, or lumbar vertebra, to act as an anchor for a connecting rod and/or to hold one or more other bony structures in place as an adjunct to spinal fusion surgery. FIG. 6 shows a schematic view of an illustrative embodiment of a bone screw 100 installed in a bony structure 601. In order to determine the desired depth and angle for placement of bone screw 100, a surgeon may use fluoroscopy and/or conventional x-ray analysis. A receiving channel is then typically drilled in the desired location and at the desired angle and bone screw 100 is inserted into the receiving channel. In the embodiment illustrated in FIG. 6, bone screw 100 is inserted into bony structure 601 until the mechanical stop formed by unthreaded portion 102 contacts surface 604 of bony structure 601. In other embodiments, unthreaded portion 102 may not form such a mechanical stop, and bone screw 100 may be inserted until unthreaded portion 102 is partially embedded in bony structure 601. In some embodiments, a rod 602 may be attached to bone screw 100 by a connecting screw 603. Rod 602 can then be used to mechanically couple bony structure 601 to an adjacent anchor, such as another bone screw (not shown) configured with a clamp fixture.

Figures 8, 9:
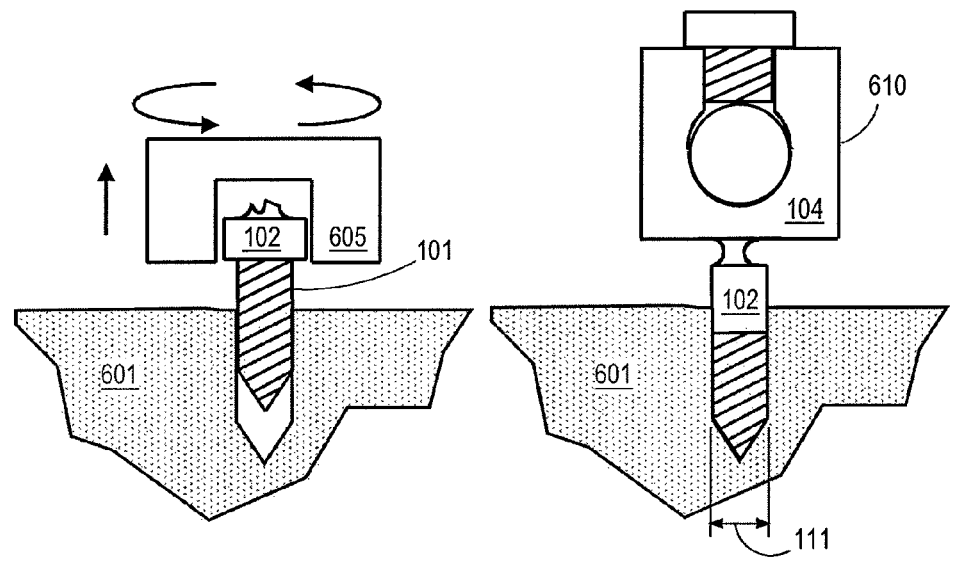
FIG. 8 shows a schematic view of an illustrative embodiment of a bone screw being removed from a bony structure after mechanical failure of the bone screw at a frangible region.
FIG. 9 shows a schematic view of an illustrative embodiment of a bone screw installed in a bony structure, in which an unthreaded portion of the screw is partially embedded in the bony structure.

FIG. 7 shows a schematic view of an illustrative embodiment of bone screw 100 installed in bony structure 601 after frangible region 103 has mechanically failed. In FIG. 7, bony structure 601 and other bony structures (not shown) treated by bone screw 100 have healed and increased in mechanical strength, but over time, e.g., after about 6 to 12 months, bone screw 100 has undergone fatigue failure. It is noted that the point of failure 701 of bone screw 100 coincides with frangible region 103. Because bony structure 601 has healed, bone screw 100 is no longer required and may be removed rather than replaced. FIG. 8 shows a schematic view of an illustrative embodiment of bone screw 100 being removed from bony structure 601 after mechanical failure of bone screw 100 at frangible region 103. Because bone screw 100 has broken at frangible region 103, unthreaded portion 102 is exposed and may be used to unscrew the screw fragment, i.e., unthreaded portion 102 and threaded portion 101, remaining in bony structure 601. A sleeved tool 605 is used to remove the screw fragment, where sleeved tool 605 is configured to match the cross section, e.g., hexagon, square, triangle, etc. of unthreaded portion 102. FIG. 9 shows a schematic view of an illustrative embodiment of a bone screw 610 installed in bony structure 601, in which unthreaded portion 102 of bone screw 100 is partially embedded in bony structure 601. In such an embodiment, the width of unthreaded portion 102 is substantially equal to major diameter 111 of threaded portion 101, i.e., only slightly larger or smaller than major diameter 111, and therefore can be substantially embedded in bony structure 601. In order to remove threaded portion 101 and unthreaded portion 102 after mechanical failure of bone screw 610 and the removal of head 104, a small amount of bony structure 601 may be removed to improve access to unthreaded portion 102. For purposes of this particular exemplary illustration, the reduced cross-section of frangible area 103 is exaggerated in FIGS. 6-9. In some embodiments, the total cross-sectional area of frangible region 103 may only be about 10% to 15% less than the cross-sectional area of unthreaded portion 102.

Figure 10:
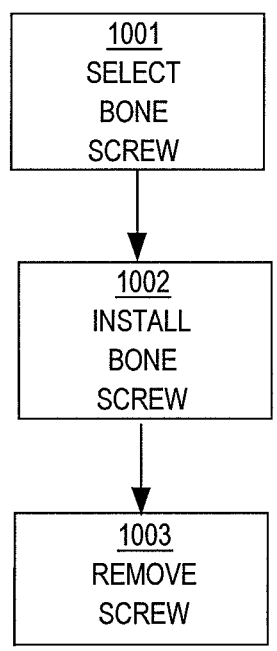
FIG. 10 shows a flow chart of an illustrative embodiment of a method of treating an injury.

FIG. 10 shows a flow chart of an illustrative embodiment of a method 1000 of treating an injury. For ease of description, method 1000 is described in terms of a bone screw substantially similar to bone screw 100 in FIG. 1. However, other configurations of bone screw may also perform method 1000. Method 1000 may include one or more operations, functions, or actions as illustrated by blocks 1001, 1002, and/or 1003. The various blocks are not intended to be limiting to the described embodiments. For example, one skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments. Prior to block 1001, traditional techniques, such as fluoroscopy or conventional x-ray analysis, may be performed to determine the depth and angle for screw placement, and an appropriate receiving channel, such as a pilot hole, may be formed in the treated bone.

In block 1001 (SELECT BONE SCREW), a bone screw 100 is selected having threaded portion 101 formed on an end of a shank, frangible region 103 formed in the shank, and unthreaded portion 102 disposed between threaded portion 101 and frangible portion 103. Unthreaded portion 102 may be configured to facilitate removal of threaded portion 101 from a bone when frangible portion 103 has broken after installation of bone screw 100 in a bone. For example, unthreaded portion 102 may have a hexagonal cross section configured to mate with the inner sleeve of a sleeved tool. In some embodiments, the selection of bone screw 100 may be based on a desired depth of insertion for bone screw 100 into the bone and a length of threaded portion 101.

In block 1002 (INSTALL BONE SCREW), bone screw 100 is inserted in the bone until threaded portion 101 is substantially embedded in the bone and at least a portion of unthreaded portion 102 is exposed outside the bone. In some embodiments, bone screw 100 may be inserted in the bone via a pilot hole. In some embodiments, unthreaded portion 102 may be configured to interfere with the circular opening formed in the bone by threaded portion 101, thereby acting as a mechanical stop. In such embodiments, unthreaded portion 102 may be wider than major diameter 111 of threaded portion 101.

In block 1003 (REMOVE SCREW FRAGMENT), a screw fragment is removed from the bone after bone screw 100 has undergone mechanical failure at frangible portion 103. In some embodiments, the screw fragment is removed from the bone using unthreaded portion 102. In some embodiments, a sleeved tool configured to fit the cross-section of unthreaded portion 102 may be used to unscrew the screw fragment from the bone. In some embodiments, a small amount of bone material may be removed around unthreaded portion 102 to provide more access thereto for the sleeved tool.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

We claim:

1. A bone screw comprising:
   a shank;
   a threaded portion formed on an end of the shank;
   a frangible region formed in the shank;
   a material disposed over the frangible region, wherein the material is an absorbable material selected to be absorbable in-vivo after installation of the screw in the bone; and
   an unthreaded portion disposed between the threaded portion and the frangible region,
   wherein the unthreaded portion is configured to facilitate removal of the threaded portion of the screw from a bone when the frangible region of the screw has broken after installation of the screw in the bone;
   wherein the frangible region is a reduced-cross-section portion of the shank;
   wherein the reduced-cross-section portion is an annular groove;
   wherein the material is selected from the group of absorbable materials consisting of calcium phosphate and calcium sulphate;
   wherein the unthreaded portion comprises at least one pair of flat and substantially parallel sides.

2. The bone screw of claim 1, wherein the unthreaded portion is hexagonal in cross section.

3. The bone screw of claim 1, wherein a cross section of the unthreaded portion is configured to interfere with a circular opening having a diameter equal to a major diameter of the threaded portion.

4. The bone screw of claim 1, wherein a diameter of the unthreaded portion is less than a minor diameter of the threaded portion.

5. The bone screw of claim 1, wherein the material disposed over the frangible region extends over the frangible region to form a surface flush with a surface of the unthreaded portion.

6. A pedicle screw comprising:
   a shank;
   a frangible region formed in the shank, wherein the frangible region is a reduced-cross-section portion of the shank;
   an absorbable material disposed over the frangible region, wherein the absorbable material is selected to be absorbable in-vivo after installation of the screw in the bone;
   a threaded portion formed on an end of the shank; and
   an unthreaded portion disposed in a center portion of the shank,
   wherein the unthreaded portion is configured to facilitate removal of the threaded portion of the screw from a bone.

\* \* \* \* \*

UNITED STATES PATENT AND TRADEMARK OFFICE
CERTIFICATE OF CORRECTION

PATENT NO. : 8,753,380 B2  
APPLICATION NO. : 13/376440  
DATED : June 17, 2014  
INVENTOR(S) : Cheng et al.

Page 1 of 1

It is certified that error appears in the above-identified patent and that said Letters Patent is hereby corrected as shown below:

On the Title Page, in Item (75), under "Inventors", in Column 1, Line 3, delete "Putuo District (CN);" and insert -- Shanghai (CN); --, therefor.

On the Title Page, in Item (56), under "OTHER PUBLICATIONS", in Column 2, Line 4, delete "internmal" and insert -- internal --, therefor.

In the Drawings

In Fig. 10, Sheet 6 of 6, insert main designator --  --, therefor.

In the Specification

In Column 1, Line 3, delete "APPLICATIONS" and insert -- APPLICATION(S) --, therefor.

In Column 2, Line 23, delete "region." and insert -- region; --, therefor.

In Column 4, Line 34, delete "rather that" and insert -- rather than --, therefor.

Signed and Sealed this  
Twenty-first Day of October, 2014

Michelle K. Lee  
*Deputy Director of the United States Patent and Trademark Office*